US010815284B2

(12) United States Patent
Lee et al.

(10) Patent No.: US 10,815,284 B2
(45) Date of Patent: Oct. 27, 2020

(54) FUSION PROTEIN COMPRISING ANTIFREEZE PROTEIN AND HUMAN EPIDERMAL GROWTH FACTOR WITH INCREASED ANTI-OXIDANT ACTIVITY AND SKIN CELL PROLIFERATION EFFECT AND COSMETIC COMPOSITION FOR ANTI-WRINKLE COMPRISING THE SAME AS EFFECTIVE COMPONENT

(71) Applicants: NEXGEN BIOTECHNOLOGIES, INC., Seoul (KR); Sun Kyo Lee, Gyeonggi-do (KR)

(72) Inventors: Sun Kyo Lee, Gyeonggi-do (KR); Tae Hyun Kim, Gyeonggi-do (KR); Seong Ran Lee, Gyeonggi-do (KR); Han Bong Ryu, Seoul (KR); Tae Won Choi, Seoul (KR); Hyeong Il Kwon, Seoul (KR); Woo Yeon Roh, Gyeonggi-do (KR)

(73) Assignees: NEXGEN BIOTECHNOLOGIES, INC., Seoul (KR); Sun Kyo Lee, Gyeonggi-Do (KR)

( * ) Notice: Subject to any disclaimer, the term of this patent is extended or adjusted under 35 U.S.C. 154(b) by 0 days.

(21) Appl. No.: 16/336,990

(22) PCT Filed: Aug. 31, 2017

(86) PCT No.: PCT/KR2017/009514
§ 371 (c)(1),
(2) Date: Mar. 27, 2019

(87) PCT Pub. No.: WO2018/062701
PCT Pub. Date: Apr. 5, 2018

(65) Prior Publication Data
US 2019/0218266 A1 Jul. 18, 2019

(30) Foreign Application Priority Data

Sep. 30, 2016 (KR) .................. 10-2016-0126114

(51) Int. Cl.
*C07K 14/485* (2006.01)
*C07K 14/46* (2006.01)
*A61Q 19/08* (2006.01)
*C12N 15/70* (2006.01)
*C12N 15/62* (2006.01)
*A61K 8/64* (2006.01)

(52) U.S. Cl.
CPC ............. *C07K 14/485* (2013.01); *A61K 8/64* (2013.01); *A61Q 19/08* (2013.01); *C07K 14/46* (2013.01); *C07K 14/461* (2013.01); *C12N 15/62* (2013.01); *C12N 15/70* (2013.01); *C07K 2319/00* (2013.01)

(58) Field of Classification Search
None
See application file for complete search history.

(56) References Cited

U.S. PATENT DOCUMENTS

| 9,321,821 | B2 * | 4/2016 | Lee | ........................ C07K 14/50 |
| 10,125,181 | B2 * | 11/2018 | Lee | ........................ A61Q 19/08 |
| 10,266,817 | B2 * | 4/2019 | Lee | ........................ A61K 8/66 |
| 10,441,632 | B2 * | 10/2019 | Lee | ........................ A61Q 19/08 |
| 2006/0008440 | A1 | 1/2006 | Blatt et al. | |
| 2016/0207962 | A1 | 7/2016 | Ba et al. | |

FOREIGN PATENT DOCUMENTS

| JP | 63-3790 A | 1/1988 |
| JP | WO 90/13571 A | 11/1990 |
| JP | 2009-203184 A | 9/2009 |
| KR | 10-1175803 B1 | 8/2012 |
| KR | 10-1482187 * | 1/2015 |
| KR | 10-2015-0056022 A | 5/2015 |
| KR | 10-1636846 * | 7/2016 |
| KR | 10-1636851 * | 7/2016 |
| KR | 10-1661912 * | 10/2016 |
| KR | 10-1678392 B1 | 11/2016 |
| WO | WO 2014202089 A2 | 12/2014 |

OTHER PUBLICATIONS

Machine translation of KR 10-1636851 (published Jul. 6, 2016).*
Machine translation of KR 10-1636846 (published Jul. 7, 2016).*
Machine translation of KR 10-1482187 (published Jan. 14, 2015).*
Machine translation of KR 10-1661912 (published Oct. 4, 2016).*
Chao et al., Protein Science (1994), 3:1760-1769.*
Ng et al., Journal of Biological Chemistry, vol. 261, No. 33, Issue of Nov. 25, pp. 15690-15695,1986.*
International Search Report for PCT/KR2017/009514 dated Dec. 11, 2017.
Zheng, Xueming et al., "Expression and Purification of Human Epidermal Growth Factor (hEGF) Fused with GB I", Biotechnology & Biotechnological Equipment, vol. 30, No. 4, Apr. 2016.
Li, Jia-Je et al., "Development and Characterization of the Recombinant Human VEGF-EGF Dual-targeting Fusion Protein as a Drug Delivery System", Bioconjugate Chemistry, vol. 26, No. 12, 2015.
Hanahan, D., "Studies on Transformation of *Escherichia coli* with Plasmids", Mol. Biol., 166, 557-580, Jan. 1983.
Carpenter G et al. "Epidermal Growth Factor" The Journal of Biological Chemistry vol. 265, 1990.
Fallon et al., "Epidermal Growth Factor Immunoreactive Material in the Central Nervous System: Location and Development" Science 224 (4653): 1107-1109, 1984.

(Continued)

*Primary Examiner* — Marianne P Allen
(74) *Attorney, Agent, or Firm* — The PL Law Group, PLLC

(57) ABSTRACT

A fusion protein has the amino acid sequence of SEQ ID NO: 5, SEQ ID NO: 6, SEQ ID NO: 7 or SEQ ID NO: 8. A composition having the fusion protein may improve skin wrinkle with increased anti-oxidant activity and skin cell proliferation effect. It can be advantageously used as a raw material of a functional cosmetic having an excellent skin regeneration effect like improvement of skin wrinkles and skin whitening.

12 Claims, 4 Drawing Sheets

Specification includes a Sequence Listing.

(56) References Cited

OTHER PUBLICATIONS

Office action dated Mar. 10, 2020 from Japan Intellectual Property Office in a counterpart Japanese Patent Application No. 2019-517042.

Li-Ming et al.,"Thermal stability Properties of an antifreeze protein from the desert beetle Microdera punctipennis", Cryobiology, vol. 60, pp. 192-197, 2010.

Nancy F.L. Ng et al., "Structure of an Antifreeze Polypeptide from the Sea Raven" J. Biol. Chemistry., vol. 267, No. 23, pp. 16069-16075, 1992.

* cited by examiner

FUSION PROTEIN COMPRISING ANTIFREEZE PROTEIN AND HUMAN EPIDERMAL GROWTH FACTOR WITH INCREASED ANTI-OXIDANT ACTIVITY AND SKIN CELL PROLIFERATION EFFECT AND COSMETIC COMPOSITION FOR ANTI-WRINKLE COMPRISING THE SAME AS EFFECTIVE COMPONENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/009514, filed Aug. 31, 2017, which claims priority to the benefit of Korean Patent Application No. 10-2016-0126114 filed in the Korean Intellectual Property Office on Sep. 30, 2016, the entire contents of which are incorporated herein by reference.

TECHNICAL FIELD

The present invention relates to a fusion protein comprising antifreeze protein and human epidermal growth factor with increased anti-oxidant activity and skin cell proliferation effect, and a cosmetic composition for improving skin wrinkle comprising the same as effective component.

BACKGROUND ART

Skin is composed of epidermis, dermis, and subcutaneous tissue. While providing protection against an attack by microbes that are introduced from an outside, skin plays a very important role for maintaining body moisture and body temperature. Epidermis plays a role of protecting skin, regulating body temperature, and maintaining body moisture, and it is composed of an extracellular matrix which is related with skin elasticity and skin flexibility. Dermis is directly related with skin aging. Skin aging is mainly caused by reduced skin elasticity and increased wrinkles resulting from denaturation of collagen fiber (collagen), elastic fiber (elastin) and mucopolysaccharide (glycosaminoglycan and mucopolysaccharide).

Upon binding to a receptor for an epidermal growth factor present on a surface of a cell, the human epidermal growth factor (hEGF) induces a dimerization of a receptor for an epidermal growth factor. A dimeric receptor for an epidermal growth factor activates the tyrosine kinase present in the receptor to induce an intracellular signal transduction system (Carpenter, G and Cohen, S, 1990, *The Journal of Biological Chemistry* 265 (14): 7790-7712). As a result of those processes, glycolysis and protein synthesis are promoted in a cell, eventually leading to cell growth (Fallon, et al., 1984, *Science* 224 (4653): 1107-1109).

Human epidermal growth factor playing an important role in skin regeneration diminishes according to a progress of aging, and the diminishing human epidermal growth factor yields a reduction in skin cell proliferation and migration, and thus causing phenomena like skin aging, increased wrinkles, and reduced skin elasticity.

An antifreeze protein (AFP) is one kind of polypeptides which enable cell growth even at sub-zero temperatures, and it has a property of preventing ice recrystallization according to binding to small ice crystals. Unlike ethylene glycol used as an antifreeze for automobiles, the antifreeze protein has an activity of maintaining osmotic pressure, transporting hormones, fatty acids, or the like, and a pH buffering agent.

Inventors of the present invention made an effort to develop a new protein for having a skin regeneration activity of human epidermal growth factor and protecting skin against active oxygen as a cause of skin aging, and as a result, it was confirmed that the antifreeze protein which has been used for easy separation of a protein exhibits an excellent effect of skin regeneration and anti-oxidation effect as it binds to human epidermal growth factor having excellent skin regeneration effect.

Incidentally, in Korean Patent Registration No. 1175803, a 'cosmetic composition for skin cell regeneration and wrinkle improvement' comprising acetyl hexapeptide-3, copper peptide, palmitoyl pentapeptide, and epidermal growth factor is disclosed, and in Korean Patent Application Publication No. 2015-0056022, a 'cosmetic composition for improving skin comprising fusion protein of epidermal grown factor' is disclosed. However, no description has been given for the fusion protein comprising antifreeze protein and human epidermal growth factor with increased anti-oxidant activity and skin cell proliferation effect, and a cosmetic composition for improving skin wrinkle comprising the same as effective component of the present invention.

SUMMARY

The present invention is devised under the circumstances described above, and the inventors of the present invention produce a novel antifreeze protein having excellent anti-oxidant activity and skin cell proliferation effect according to fusion of a human epidermal growth factor protein, which is known to have an excellent cell regeneration effect, to an antifreeze protein from sea raven or ocean pout. Compared to a treatment with the human epidermal growth factor protein alone, the fusion protein not only exhibits a high free radical scavenging activity but also has an excellent cell proliferation effect for skin fibroblasts. As a result of carrying out a skin test after preparing various cosmetic formulations, the wrinkle improving and skin whitening effect was confirmed from the testees, and the present invention is completed accordingly.

To solve the problems described above, the present invention provides a fusion protein of antifreeze protein and human epidermal growth factor having increased anti-oxidant activity and skin cell proliferation effect.

The present invention also provides a gene encoding the aforementioned fusion protein.

The present invention also provides a recombinant vector comprising the aforementioned gene.

The present invention also provides a host cell transformed with the aforementioned recombinant vector.

The present invention also provides a method for producing in a host cell a fusion protein of antifreeze protein and human epidermal growth factor including transforming a host cell with the aforementioned recombinant vector to overexpress a gene encoding a fusion protein of antifreeze protein and human epidermal growth factor.

The present invention also provides a fusion protein of antifreeze protein and human epidermal growth factor produced by the production method.

The present invention also provides a cosmetic composition for improving skin wrinkle comprising, as an effective component, the fusion protein of antifreeze protein and human epidermal growth factor.

As the fusion protein of antifreeze protein and human epidermal growth factor of the present invention has an excellent anti-oxidation activity and exhibits an excellent cell proliferation effect for skin fibroblasts, it can be advantageously used as a raw material of an anti-aging cosmetic composition having excellent skin regeneration effect like improvement of skin wrinkles and skin whitening.

Figure 1:
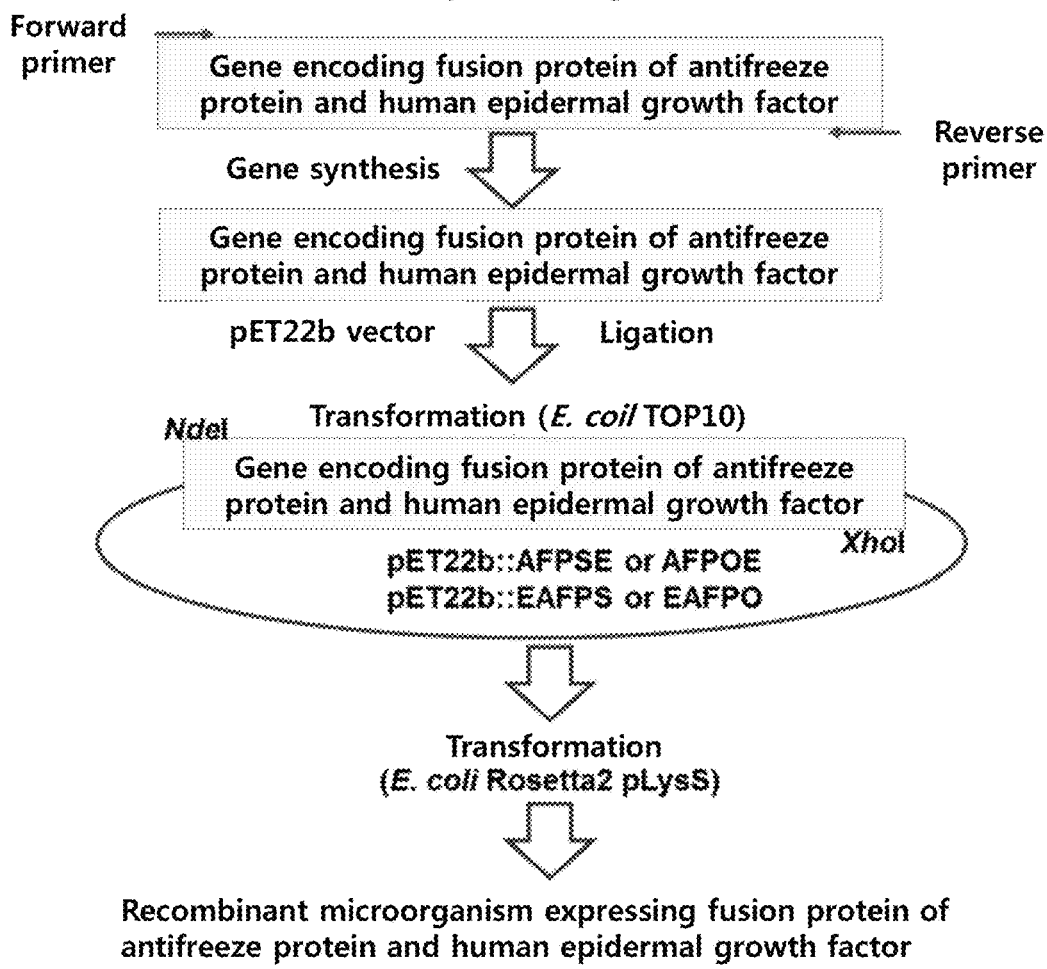
FIG. 1 is a schematic diagram illustrating the preparation and transformation of a recombinant plasmid containing a gene encoding a fusion protein of antifreeze protein and human epidermal growth factor (pET22b::AFPSE or pET22b::AFPOE and pET22b::EAFPS or pET22b::EAFPO). AFPSE, antifreeze protein from sea raven (AFPSR)-human epidermal growth factor (EGF) fusion protein; AFPOE, antifreeze protein from ocean pout (AFPOP)-EGF fusion protein; EAFPS, EGF-AFPSR fusion protein; EAFPO, EGF-AFPOP fusion protein.

To achieve the object of the present invention, the present invention provides a fusion protein of antifreeze protein and human epidermal growth factor having increased anti-oxidant activity and skin cell proliferation effect.

The antifreeze protein of the present invention can be an antifreeze protein from sea raven (AFPSR) or an antifreeze protein from ocean pout (AFPOP), but it is not limited thereto.

The fusion protein according to the present invention is a fusion protein having fusion between the antifreeze protein from sea raven (AFPSR) and human epidermal growth factor (EGF) or a fusion protein having fusion between the antifreeze protein from ocean pout (AFPOP) and human epidermal growth factor.

With regard to the fusion protein of the present invention, scope of the fusion protein of antifreeze protein derived from sea raven and human epidermal growth factor includes a protein having the amino acid sequence represented by SEQ ID NO: 5 (AFPSR-EGF) or SEQ ID NO: 6 (EGF-AFPSR), and also functional equivalents of the protein. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 5 or SEQ ID NO: 6, and it indicates a protein exhibiting substantially the same activity as the fusion protein represented by SEQ ID NO: 5 or SEQ ID NO: 6. The expression "substantially the same activity" means an antioxidant activity and a skin cell proliferation effect.

With regard to the fusion protein of the present invention, the fusion protein obtained by fusion of an antifreeze protein from sea raven to the amino terminal of a human epidermal growth factor (i.e., AFPSR-EGF) preferably consists of the amino acid sequence of SEQ ID NO: 5, and it may be a novel protein which is produced by fusion between the antifreeze protein from sea raven consisting of the $1^{st}$ to the $130^{th}$ amino acids and the human epidermal growth factor protein consisting of the $131^{st}$ to the $183^{rd}$ amino acids of the above amino acid sequence. Furthermore, the fusion protein obtained by fusion of an antifreeze protein from sea raven to the carboxy terminal of a human epidermal growth factor (i.e., EGF-AFPSR) preferably consists of the amino acid sequence of SEQ ID NO: 6, and it may be a novel protein which is produced by fusion between the human epidermal growth factor protein consisting of the $1^{st}$ to the $54^{th}$ amino acids and the antifreeze protein from sea raven consisting of the $55^{th}$ to the $183^{rd}$ amino acids of the above amino acid sequence.

With regard to the fusion protein of the present invention, scope of the fusion protein of antifreeze protein derived from ocean pout and human epidermal growth factor includes a protein having the amino acid sequence represented by SEQ ID NO: 7 (AFPOP-EGF) or SEQ ID NO: 8 (EGF-AFPOP), and also functional equivalents of the protein. The term "functional equivalent" indicates a protein having, as a result of addition, substitution, or deletion of an amino acid, at least 70%, preferably at least 80%, more preferably at least 90%, and even more preferably at least 95% sequence homology with the amino acid sequence represented by SEQ ID NO: 7 or SEQ ID NO: 8, and it indicates a protein exhibiting substantially the same activity as the fusion protein represented by SEQ ID NO: 7 or SEQ ID NO: 8. The expression "substantially the same activity" is the same as described above.

With regard to the fusion protein of the present invention, the fusion protein obtained by fusion of an antifreeze protein from ocean pout to the amino terminal of a human epidermal growth factor (i.e., AFPOP-EGF) preferably consists of the amino acid sequence of SEQ ID NO: 7, and it may be a novel protein which is produced by fusion between the antifreeze protein from ocean pout consisting of the $1^{st}$ to the $66^{th}$ amino acids and the human epidermal growth factor protein consisting of the $67^{th}$ to the $119^{th}$ amino acids of the above amino acid sequence. Furthermore, the fusion protein obtained by fusion of an antifreeze protein from ocean pout to the carboxy terminal of a human epidermal growth factor (i.e., EGF-AFPOP) preferably consists of the amino acid sequence of SEQ ID NO: 8, and it may be a novel protein which is produced by fusion between the human epidermal growth factor protein consisting of the $1^{st}$ to the $54^{th}$ amino acids and the antifreeze protein from ocean pout consisting of the $55^{th}$ to the $119^{th}$ amino acids of the above amino acid sequence.

The present invention further provides a gene encoding the fusion protein. The gene may consist of the nucleotide sequence of SEQ ID NO: 1 (AFPSR-EGF), SEQ ID NO: 2 (EGF-AFPSR), SEQ ID NO: 3 (AFPOP-EGF), or SEQ ID NO: 4 (EGF-AFPOP), which are all *E. coli* codon-optimized, but the gene is not limited thereto.

This gene encoding the fusion protein according to the present invention may include the nucleotide sequence of SEQ ID NO: 1, SEQ ID NO: 2, SEQ ID NO: 3, or SEQ ID NO: 4. Furthermore, homologues of the nucleotide sequence are also within the scope of the present invention. Specifically, the above described gene may comprise a nucleotide sequence which has preferably at least 70%, more preferably at least 80%, still more preferably at least 90%, and most preferably at least 95% homology with the nucleotide sequence selected from a group consisting of SEQ ID NO: 1, SEQ ID NO: 2, SEQ ID NO: 3, and SEQ ID NO: 4. The "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

"Codon optimization" means a modification of codon of a polynucleotide encoding a protein with a codon that is used first than others in a specific organism such that the coded protein can be more efficiently expressed therein. Because most amino acids are described by several codons that are referred to as "synonym" or "synonymous codon", genetic codes have degeneracy. However, codon usage by a specific organism is not random, and it is rather biased to specific codon triplets. Such codon usage bias may be even higher in relation with a certain gene, a gene with common function or ancestor origin, protein expressed at high level vs. proteins with low copy number, or a group protein coding region of a genome of an organism. The nucleotide sequence of SEQ ID NO: 1, SEQ ID NO: 2, SEQ ID NO: 3, or SEQ ID NO: 4 of the present invention is a sequence which has been optimized to *E. coli* codon such that the gene encoding the fusion protein of human epidermal growth factor and antifreeze protein can be expressed in *E. coli*.

The present invention further provides a recombinant vector comprising the gene encoding the fusion protein of human epidermal growth factor and antifreeze protein and a host cell transformed with the recombinant vector.

The term "recombinant" indicates a cell which replicates a heterogeneous nucleotide or expresses said nucleotide, or a peptide, a heterogeneous peptide, or a protein encoded by a heterogeneous nucleotide. Recombinant cell can express a gene or a gene fragment in the form of a sense or antisense, which are not found in natural state of cell. In addition, a recombinant cell can express a gene that is found in natural state, provided that said gene is modified and re-introduced into the cell by an artificial means.

According to the present invention, the gene encoding the fusion protein of human epidermal growth factor and antifreeze protein can be inserted to a recombinant expression vector. The term "recombinant expression vector" means bacteria plasmid, phage, yeast plasmid, plant cell virus, mammalian cell virus, or other vector. Any plasmid and vector can be generally used if it can replicate and is stabilized in a host. Important characteristics of the expression vector include that it comprises a replication origin, a promoter, a marker gene, and a translation control element.

The expression vector comprising the gene sequence encoding the fusion protein of human epidermal growth factor and antifreeze protein and an appropriate signal for regulating transcription/translation can be constructed according to a method which is well known to a skilled person in the art. The method includes an in vitro recombinant DNA technique, a DNA synthesis technique, and an in vivo recombinant technique. For inducing mRNA synthesis, the DNA sequence can be effectively linked to a suitable promoter present in the expression vector. In addition, the expression vector may comprise a ribosome binding site as a translation initiation site and a transcription terminator.

The recombinant vector according to one embodiment of the present invention is prepared by in-frame fusion of 5' terminal (NdeI restriction enzyme site) and 3' terminal (XhoI restriction enzyme site) of a synthesized gene encoding the fusion protein of human epidermal growth factor and antifreeze protein to pET22b vector, and it is a vector characterized in that it can produce the fusion protein of human epidermal growth factor and antifreeze protein based on effective expression of the aforementioned gene with an aid of lac promoter (lac promoter) and lacI repressor (lacI repressor).

For a host cell having an ability of having stable and continuous cloning and expression of the vector of the present invention in a prokaryotic cell, any host cell known in the pertinent art can be used. Examples of the prokaryotic cells include, *Bacillus* sp. strain including *E. coli* Rosetta, *E. coli* JM109, *E. coli* BL21, *E. coli* RR1, *E. coli* LE392, *E. coli* B, *E. coli* X 1776, *E. coli* W3110, *Bacillus subtillus*, *Bacillus thuringiensis* and the like, and intestinal bacteria and strains including *Salmonella typhimurium*, *Serratia marcescens* and various *Pseudomonas* sp. etc.

Furthermore, when an eukaryotic cell is transformed with the vector of the present invention, yeast (*Saccharomyce cerevisiae*), an insect cell, a human cell (for example, CHO (Chinese hamster ovary) cell line, W138, BHK, COS-7, 293, HepG2, 3T3, RIN, and MDCK cell line), a plant cell, and the like can be used as a host cell.

The host cell transformed with the recombinant vector according to one embodiment of the present invention is preferably *E. coli*, and more preferably *E. coli* Rosetta2 (DE3) pLysS, but not limited thereto.

When a host cell is a prokaryotic cell, delivery of the vector of the present invention into a host cell can be carried out by $CaCl_2$) method, Hanahan's method (Hanahan, D., *J. Mol. Biol.*, 166:557-580 (1983)) or an electroporation method, and the like. In addition, when a host cell is an eukaryotic cell, the vector can be introduced to a host cell by a microinjection method, calcium phosphate precipitation method, an electroporation method, a liposome-mediated transfection method, DEAE-dextran treatment method, or a gene bombardment method, and the like.

The present invention further provides a method for producing in a host cell a fusion protein of antifreeze protein and human epidermal growth factor including transforming a host cell with the recombinant vector of the present invention to overexpress a gene encoding a fusion protein of antifreeze protein and human epidermal growth factor.

In the method according to one embodiment of the present invention, the host cell may be preferably *E. coli*, and more preferably *E. coli* Rosetta2 (DE3) pLysS, but not limited thereto.

The present invention further provides a fusion protein of human epidermal growth factor and antifreeze protein produced by the production method of the present invention.

The present invention further provides a cosmetic composition for improving skin wrinkle comprising, as an effective component, a fusion protein of antifreeze protein and human epidermal growth factor having skin regeneration effect and excellent anti-oxidant activity.

As the cosmetic composition of the present invention comprises, as an effective component, a fusion protein of antifreeze protein and human epidermal growth factor having skin regeneration effect and excellent anti-oxidant activity, it is a cosmetic composition which has an effect of improving skin wrinkles and skin whitening based on skin cell generation and also an anti-aging activity.

In the cosmetic composition according to one embodiment of the present invention, content of the fusion protein is preferably 0.0001 to 1.0% by weight relative to the total weight of the cosmetic composition.

If the protein content is lower than 0.0001% by weight, the effect is not obtained as the anti-oxidant activity is not exhibited in skin. On the other hand, if the protein content is higher than 1.0% by weight, the enhanced effect may be insignificant compared to the increase in content.

In the cosmetic composition of the present invention, components that are typically used for a cosmetic composition are included in addition to the effective components that are described above. Examples thereof include a lipid material, an organic solvent, a dissolution agent, a condensation agent, a gelling agent, a softening agent, an anti-oxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic or liphophilic activating agent, a common auxiliary agent such as lipid vesicle, and a carrier.

The composition of the present invention can be prepared in any formulation which is generally prepared in the pertinent art. For example, the composition may be formulated into a solution, a suspension, an emulsion, a paste, a gel, a crème, a lotion, a powder, an oil, a powder foundation, an emulsion foundation, a wax foundation, a spray, or the like, but not limited thereto. More specifically, the composition may be formulated into a skin, a skin softener, a skin toner, an astringent, a lotion, a milk lotion, a moisture lotion, a nutrition lotion, a massage crème, a nutrition crème, an eye crème, a moisture crème, a hand crème, an essence, a nutrition essence, a pack, a cleansing foam, a cleansing water, a cleansing lotion, a cleansing crème, a body lotion, a body cleanser, a soap, a powder, or the like.

In a case in which the cosmetic composition of the present invention has a formulation type of paste, crème, or gel, it is possible to use, as a carrier component, animal oil, plant oil, wax, paraffin, starch, tragacanth, cellulose derivatives, polyethylene glycol, silicone, bentonite, silica, talc, or zinc oxide.

In a case in which the cosmetic composition of the present invention has a formulation type of powder or spray, it is possible to use, as a carrier component, lactose, talc, silica, aluminum hydroxide, calcium silicate, or polyamide powder, when it is spray, in particular, a propellant such as chlorofluoro hydrocarbon, propane/butane, or dimethyl ether may be additionally contained.

In a case in which the cosmetic composition of the present invention has a formulation type of solution or emulsion, a solvent, a dissolution agent, or an emulsifier is used as a carrier component, and examples thereof include water, ethanol, isopropyl alcohol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation type of suspension, it is possible to use, as a carrier component, a liquid phase diluent such as water, ethanol, or propylene glycol, a suspension agent such as ethoxylated isostearyl alcohol, polyoxyethylene sorbitol ester, or polyoxyethylene sorbitan ester, microcrystalline cellulose, aluminum metahydroxide, bentonite, agar, or tragacanth.

Hereinbelow, the present invention is explained in greater detail in view of the Examples. However, it is evident that the following Examples are given only for exemplification of the present invention and by no means the present invention is limited to the following Examples.

EXAMPLES

Example 1. Preparation of Recombinant Expression Vector and Transformed Recombinant Microorganism for Producing Fusion Protein of Antifreeze Protein and Human Epidermal Growth Factor The optimized gene encoding the fusion protein including antifreeze protein from sea raven (AFPSR) or antifreeze protein from ocean pout (ASPOP) and human epidermal growth factor (EGF), recombinant expression vector, and transformed recombinant microorganism were prepared according to the following method. By using as a template the gene encoding the fusion protein of antifreeze protein from sea raven and human epidermal growth factor or the fusion protein of antifreeze protein from ocean pout and human epidermal growth factor, a fragment of the gene (SEQ ID NO: 1 or SEQ ID NO: 2) encoding a fusion protein (SEQ ID NO: 5 or SEQ ID NO: 6) of antifreeze protein from sea raven and human epidermal growth factor in which 183 amino acids are encoded and a fragment of the gene (SEQ ID NO: 3 or SEQ ID NO: 4) encoding a fusion protein (SEQ ID NO: 7 or SEQ ID NO: 8) of antifreeze protein from ocean pout and human epidermal growth factor in which 119 amino acids are encoded, in which both genes are optimized for expression in a host microorganism, were synthetically prepared. The primers used therefor are as described below.

The primers for the synthesis of a fusion protein including the antifreeze protein from sea raven and human epidermal growth factor protein are as follows.

```
Forward primer:
                                    (SEQ ID NO: 9)
5'-ATACATATGCAGCGTGCA-3'

Reverse primer:
                                    (SEQ ID NO: 10)
5'-GTGCTCGAGGCGCAACTC-3'

Sense primer:
                                    (SEQ ID NO: 11)
5'-CGCCATGACTTTCAACTCAGACTC-3'

Antisense primer:
                                    (SEQ ID NO: 12)
5'-GTGTCTGAGTTGAAAGTCATGGCG-3'
```

The primers for the synthesis of a fusion protein including the antifreeze protein from ocean pout and human epidermal growth factor protein are as follows.

```
Forward primer:
                                    (SEQ ID NO: 13)
5'-ATACATATGAACCAGGCA-3'

Reverse primer:
                                    (SEQ ID NO: 14)
5'-TGCTCGAGGCGCAAC-3'
```

```
-continued
Sense primer:
                              (SEQ ID NO: 15)
5'-TACGCGGCTAACTCAGAC-3'

Antisense primer:
                              (SEQ ID NO: 16)
5'-GTCTGAGTTAGCCGCGTA-3'
```

The above gene fragment and recombinant plasmid were digested and inserted by using the same restriction enzymes (5' terminal NdeI restriction enzyme site (CATATG) and 3' terminal XhoI restriction enzyme site (CTCGAG)), and thus the recombinant plasmid shown in FIG. 1 (pET22b pET22b::AFPSE or AFPOE; pET22b::EAFPS or EAFPO) was prepared. *E. coli* TOP10 was then transformed with each of the recombinant plasmid (pET22b::AFPSE or AFPOE; pET22b::EAFPS or EAFPO) product which has been prepared above so that a gene construct was obtained in large amount from the host microorganism.

*E. coli* Rosetta2 (DE3) pLysS (Novagen) was transformed with each of the recombinant plasmid (pET22b::AFPSE or AFPOE; pET22b::EAFPS or EAFPO) product which has been prepared above, and thus a recombinant microorganism for producing a fusion protein of antifreeze protein and human epidermal growth factor, in which the gene construct is inserted to the host microorganism, was prepared. A diagram with further details is given in FIG. 1.

Example 2. Expression Induction and Separation of Fusion Protein of Antifreeze Protein and Human Epidermal Growth Factor

*E. coli* Rosetta2 (DE3) pLysS (Novagen, Germany) prepared in Example 1 as *E. coli* for expressing the fusion protein of antifreeze protein and human epidermal growth factor was cultured till to have $OD_{600}$=0.6 to 0.8 when it was batch-cultured using 1 L LB or BSB medium or $OD_{600}$=15 to 20 when it was continuously cultured using a 20 L fermenter. After that, each of them was added with 1 to 5 mM (final concentration) IPTG or 2% (final concentration) lactose to induce the expression of the genes in clone. After further culture for 4 hours to 5 hours, the cells were collected by centrifuge. The cells were completely suspended in a buffer solution (phosphate buffered saline, NaCl 8 g, KCl 0.2 g, $Na_2HPO_4$ 1.44 g, $KH_2PO_4$ 0.24 g/L, pH 7.4), and the cells were disrupted by using an ultrasonic homogenizer. Accordingly, a solution containing intracellular proteins was separated.

Thereafter, the fusion protein of antifreeze protein and human epidermal growth factor was passed through a nickel-agarose column at a rate of 1 to 3 mL/min. Subsequently, the column was washed several times with a buffer solution for binding, and each of 50, 100, and 250 mM imidazole solutions (pH 7.4) was applied to the column to have fractionation elution of the fusion protein of antifreeze protein and human epidermal growth factor from the column, and thus the fusion protein was purified.

Figure 2:
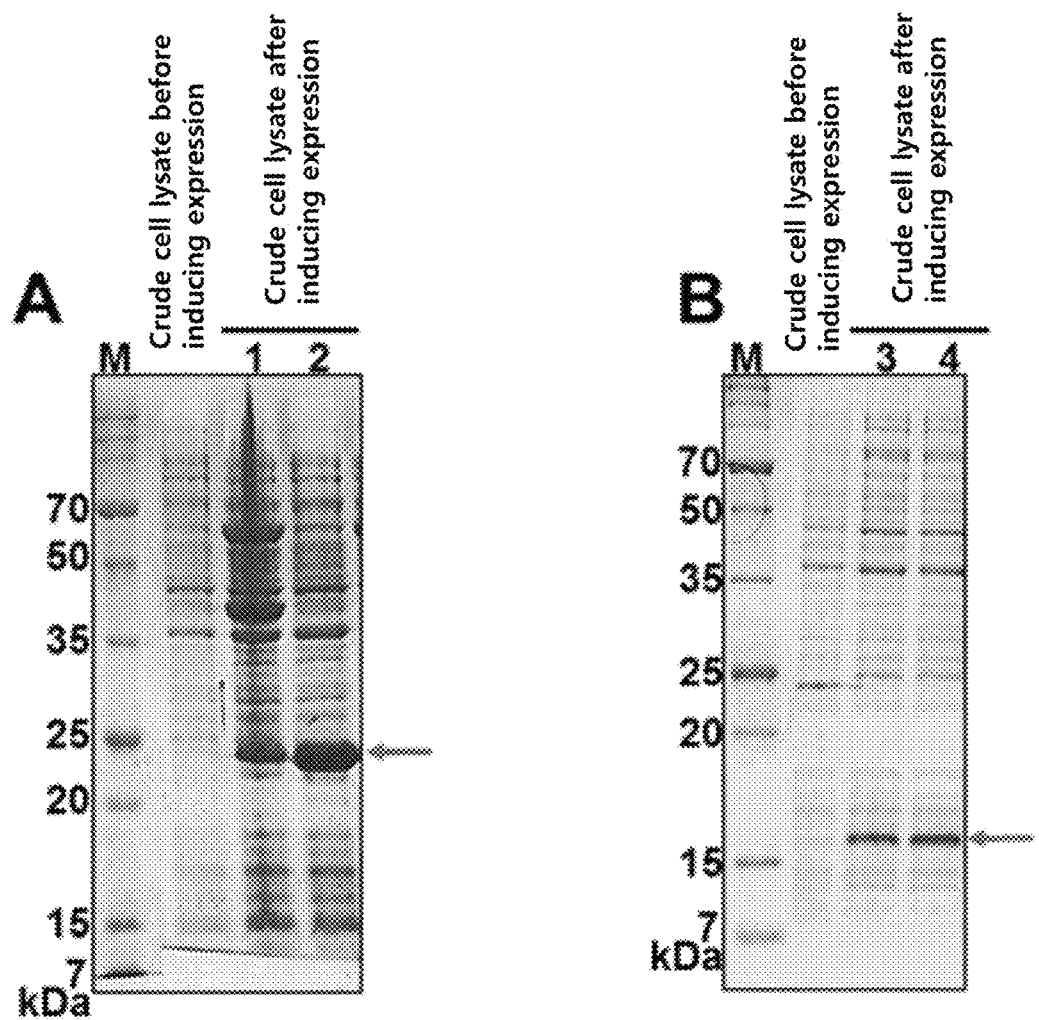
FIG. 2 shows the result of determining the expression of a fusion protein of antifreeze protein (A of FIG. 2) and human epidermal growth factor (B of FIG. 2) in *E. coli*, in which the determination is made by using SDS-polyacrylamide gel. M, protein size marker; crude cell lysate before inducing expression; crude cell lysate after inducing expression; 1, AFPSE (AFPSR-EGF); 2, EAFPS (EGF-AFPSR); 3, AFPOE (AFPOP-EGF); 4, EAFPO (EGF-AFPOP).

FIG. 2 shows the result of determining the expression of a fusion protein of antifreeze protein and human epidermal growth factor in *E. coli*, in which the determination is made by using 15% SDS-polyacrylamide gel. As a result, it was confirmed that, by a treatment with IPTG or lactose, induced expression of the fusion protein of antifreeze protein and human epidermal growth factor in cells of *E. coli* is obtained.

Example 3. Skin Cell Proliferation Effect of Fusion Protein of Antifreeze Protein and Human Epidermal Growth Factor After collecting a sample from a separated and purified fraction from which the presence of a fusion protein of antifreeze protein and human epidermal growth factor has been confirmed in Example 2, the cell proliferation effect for skin fibroblasts (i.e., Human Dermal Fibroblasts adult, HDFa cell) was determined.

In order to measure the activity of a fusion protein of antifreeze protein and human epidermal growth factor, cultured skin fibroblasts were treated with the fusion protein of antifreeze protein and human epidermal growth factor at a concentration of 0.02 ppm, 0.2 ppm, 2 ppm, or 20 ppm, and then cultured for 3 days at 37° C. After that, the existence or non-existence of the cell proliferation was determined based on crystal violet staining method.

Figure 3:
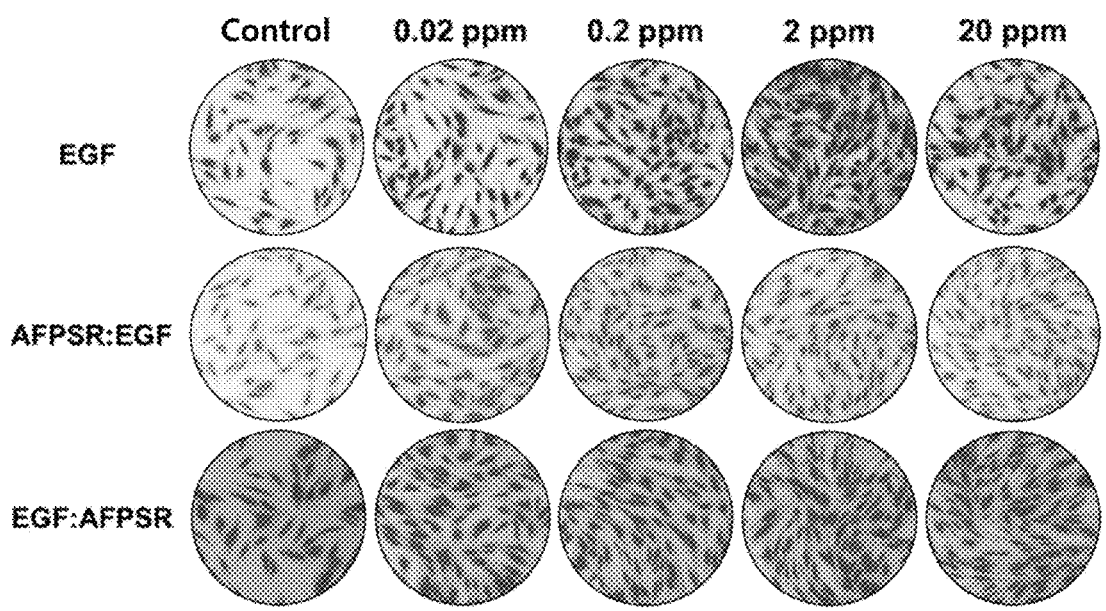
FIG. 3 is a photographic image for determining the cell proliferation effect on skin fibroblasts according to a treatment of skin fibroblasts (adult human dermal fibroblasts, HDFa cell) with a fusion protein of antifreeze protein derived from sea raven and human epidermal growth factor after the isolation of the fusion protein.

As a result, it was found that a higher cell proliferation effect is observed from the fusion protein of antifreeze protein from sea raven and human epidermal growth factor (i.e., AFPSR:EGF, EGF:AFPSR of FIG. 3) compared to the group treated with a single protein (e.g., EGF of FIG. 3). In this regard, EGF inside the fusion protein corresponds to, instead of a full-length protein, an active domain used for production of a fusion protein with antifreeze protein and, in case of a treatment with EGF only or a fusion protein of EGF and antifreeze protein at same concentration (e.g., 0.02 ppm), mole number of the fusion protein would be about ½ of EGF.

As such, if a similar skin fibroblast proliferation effect is exhibited at the same concentration, it is recognized that the fusion protein of antifreeze protein and human epidermal growth factor has the skin fibroblast proliferation effect that is about 2 times higher than EGF. As it can be recognized from FIG. 3, compared to EGF, the number of skin fibroblasts is higher when the treatment is carried out with the fusion protein of antifreeze protein and human epidermal growth factor, and thus the fusion protein is found to have a skin fibroblast proliferation effect that is 2 times or higher than EGF. Based on this result, it is believed that the fusion protein of antifreeze protein and human epidermal growth factor has an increased skin cell proliferation effect.

Figure 4:
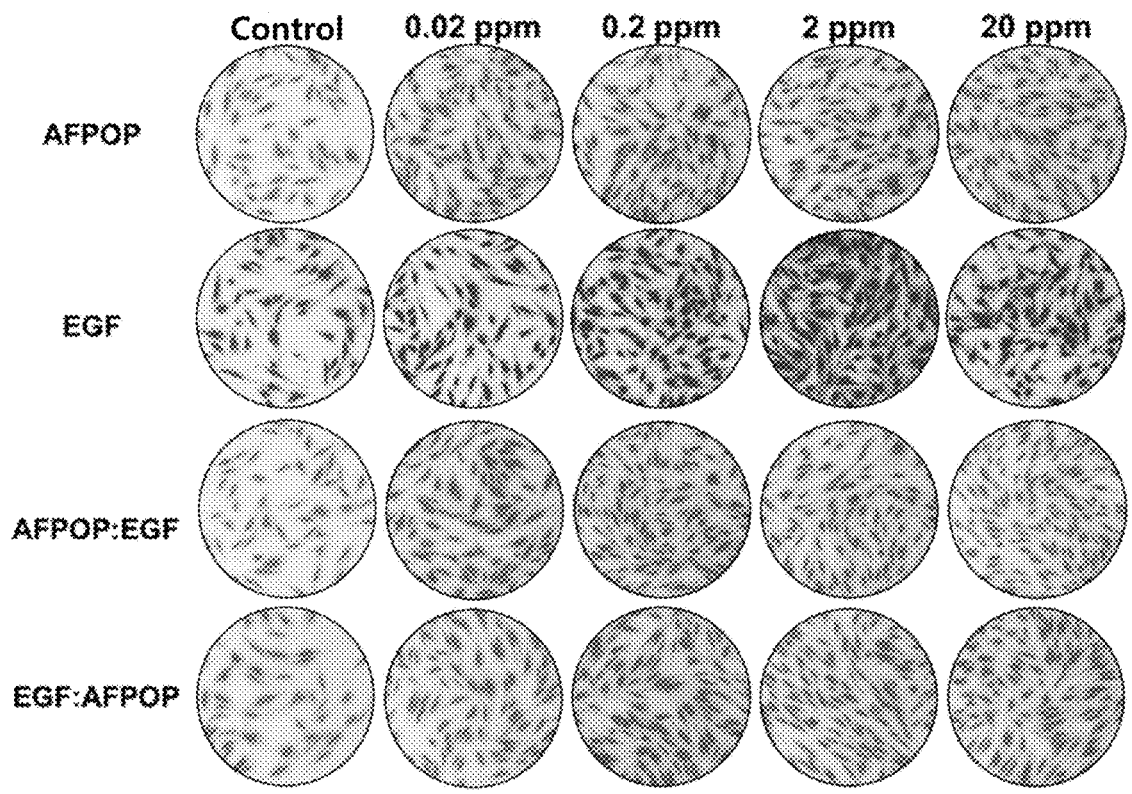
FIG. 4 is a photographic image for determining the cell proliferation effect on skin fibroblasts according to a treatment of skin fibroblasts with a fusion protein of antifreeze protein derived from ocean pout and human epidermal growth factor after the isolation of the fusion protein.

Furthermore, it was found that a higher cell proliferation effect is observed from the fusion protein of antifreeze protein from ocean pout and human epidermal growth factor (i.e., AFPOP:EGF, EGF:AFPOP of FIG. 4) compared to the group treated with a single protein (e.g., EGF, AFPOP of FIG. 4). In this regard, as it has been described above, EGF and AFPOP inside the fusion protein correspond to each active domain used for production of a fusion protein instead of a full-length protein of each, and, in case of a treatment with EGF or AFPOP only or a fusion protein of human epidermal growth factor and antifreeze protein at same concentration (e.g., 0.02 ppm), mole number of the fusion protein would be about ½ of each of EGF and AFPOP.

As such, if a similar skin fibroblast proliferation effect is exhibited at the same concentration, it is recognized that the fusion protein of antifreeze protein and human epidermal growth factor has the skin fibroblast proliferation effect that is about 2 times higher than each of EGF and AFPOP. As it can be recognized from FIG. 4, compared to each of EGF and AFPOP, the number of skin fibroblasts is higher when the treatment is carried out with the fusion protein of antifreeze protein and human epidermal growth factor, and thus the fusion protein is found to have a skin fibroblast proliferation effect that is 2 times or higher than EGF. Based on this result, it is believed that the fusion protein of antifreeze protein and human epidermal growth factor has an increased skin cell proliferation effect.

Example 4. Anti-Oxidant Effect of Fusion Protein of Antifreeze Protein and Human Epidermal Growth Factor In order to measure the anti-oxidant effect of a fusion protein of antifreeze protein and human epidermal growth factor, the DPPH method (1,1-diphenyl-2-pycryl-hydrazyl method), which is one of the methods for measuring a free radical scavenging effect, was used. This reagent is present as a relatively stable free radical, and the DPPH method is one of the in vitro methods that are primarily used in general to confirm the free radical scavenging effect.

Figure 5:
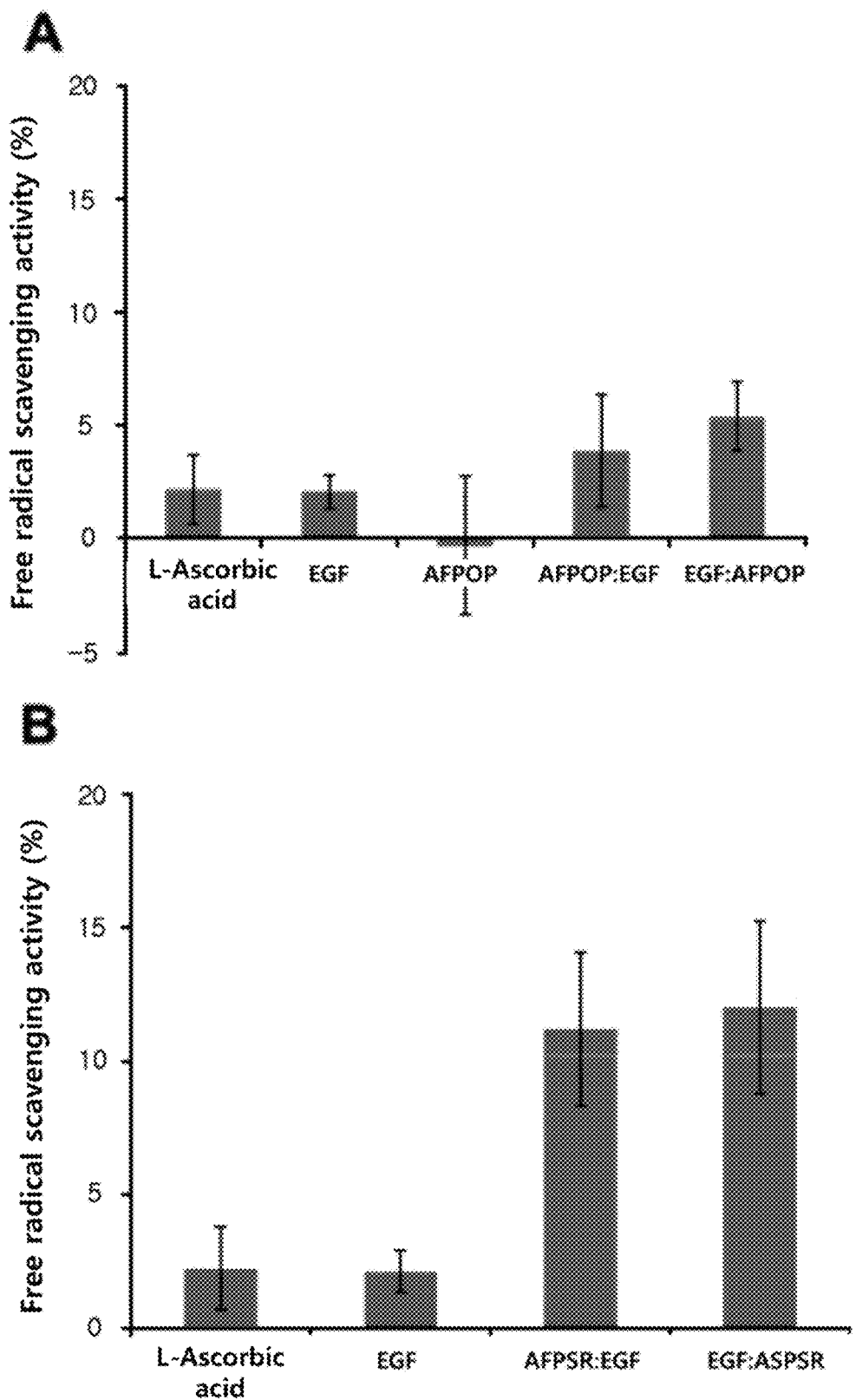
FIG. 5 shows a result of DPPH test which has been carried out to determine the anti-oxidative effect of a fusion protein of antifreeze protein (A of FIG. 5) and human epidermal growth factor (A of FIG. 5).

In order to see the anti-oxidation effect of the fusion protein of antifreeze protein and human epidermal growth factor, L-ascorbic acid was used as a control group. For the test, the fusion protein of antifreeze protein and human epidermal growth factor and L-ascorbic acid were prepared each at 1 µM concentration while DPPH was prepared at concentration of 0.2 mM. After mixing each of them at a ratio of 1:1, they were allowed to stand for 30 minutes at 37° C. After that, the absorbance was measured by using 520 nm ELISA reader. The free radical scavenging activity (%) was calculated based on the following equation 1, and the results are shown in FIG. 5.

$$\text{Free radical scavenging activity (\%)} = 100 - ((B/A) *100) \quad \text{[Equation 1]}$$

A: Absorbance by control group which has not been treated with any test sample
B: Absorbance by test group which has been treated with test sample As a result, it was shown that the fusion protein of antifreeze protein and human epidermal growth factor showed the free radical scavenging activity that is about 2 to 4 times higher than that of the L-ascorbic acid control group. As such, it was found that the fusion protein of antifreeze protein and human epidermal growth factor of the present invention has a high anti-oxidant effect, and this result indicates that the fusion protein has an effect of preventing skin aging based on the anti-oxidant effect.

Test Example 1. Sensory Skin Irritation Test Regarding Skin Regeneration Activity Like Wrinkle Improvement and Skin Whitening, and Anti-Oxidant Effect Cosmetic compositions of Preparation examples 1, 2, 3, and 4, in which the fusion protein (AFPSR-EGF) of antifreeze protein from sea raven and human epidermal growth factor separated and purified in Example 1 is contained as an effective component, and cosmetic compositions of Comparative example 1, 2, 3, and 4 were prepared and used for a sensory test.

Specifically, in order to determine an anti-wrinkle effect among the items relating to skin regeneration activity, total 30 people including men and women between the age of 30 and 59 (i.e., 10 people in 30 s, 10 people in 40 s, and 10 people in 50 s) were selected as a subject, and they were asked to apply the control group (Comparative example) to the area around the left eye or the test group (Preparation example) to the area around the right eye, once a day for 2 weeks continuously. The evaluation was carried out in terms of wrinkle smoothing around eye. Furthermore, with regard to the skin whitening as one of the activity-related items described above, the degree of a change in skin tone was also evaluated in the same manner as above. Furthermore, as for the anti-oxidation-related matter, the anti-aging effect was analyzed as an aging retardation effect, and relative comparison was made based on naked eye observation. As for the skin irritation, the sensory test was also carried out in the same manner as above regarding itchiness, stinging feeling, erythema of skin or the like. The evaluation was carried out based on the following evaluation criteria, i.e., 5-point scale including quite excellent (5 points), excellent (4 points), favorable (3 points), poor (2 points), and very poor (1 point).

Preparation Example 1 and Comparative Example 1

By adding or not adding, as an effective component, the fusion protein (AFPSR-EGF) of antifreeze protein from sea raven and human epidermal growth factor, a skin composition was prepared with the components and content that are described in the following Table 1.

TABLE 1

| | Skin composition | |
|---|---|---|
| Component | Preparation example 1 (% by weight) | Comparative example 1 (% by weight) |
| AFPSR-EGF | 0.002 | — |
| Amino acid stock | 0.1 | 0.1 |
| Mineral mixture | 0.0007 | 0.0007 |
| Purified water | q.s. | q.s. |

The sensory test results using Preparation example 1 and Comparative example 1 of above Table 1 are as shown in the following Table 2.

TABLE 2

| | | Sensory test result of Preparation example 1 and Comparative example 1 | | | | |
|---|---|---|---|---|---|---|
| | | Skin regeneration | | | | Skin irritation |
| | | Wrinkle improvement | | Skin whitening | | |
| | No. | Preparation example 1 | Comparative example 1 | Preparation example 1 | Comparative example 1 | Preparation example 1 |
| 30 s | 1 | 4 | 3 | 4 | 3 | 4 |
| | 2 | 4 | 3 | 4 | 3 | 5 |
| | 3 | 4 | 3 | 3 | 3 | 4 |
| | 4 | 4 | 3 | 3 | 3 | 4 |
| | 5 | 3 | 2 | 3 | 2 | 3 |
| | 6 | 4 | 2 | 4 | 3 | 4 |
| | 7 | 4 | 3 | 4 | 3 | 4 |
| | 8 | 3 | 2 | 4 | 3 | 4 |
| | 9 | 4 | 2 | 4 | 3 | 5 |
| | 10 | 3 | 3 | 4 | 3 | 4 |
| 40 s | 11 | 4 | 2 | 5 | 3 | 4 |
| | 12 | 4 | 2 | 5 | 2 | 4 |
| | 13 | 4 | 2 | 4 | 3 | 5 |
| | 14 | 4 | 3 | 5 | 2 | 5 |
| | 15 | 5 | 2 | 4 | 2 | 5 |
| | 16 | 4 | 3 | 4 | 2 | 4 |
| | 17 | 5 | 2 | 5 | 2 | 5 |
| | 18 | 4 | 3 | 4 | 3 | 5 |
| | 19 | 4 | 3 | 4 | 3 | 5 |
| | 20 | 4 | 3 | 5 | 2 | 4 |
| 50 s | 21 | 5 | 2 | 4 | 3 | 5 |
| | 22 | 5 | 2 | 5 | 2 | 5 |
| | 23 | 5 | 2 | 5 | 2 | 5 |
| | 24 | 4 | 3 | 4 | 2 | 5 |
| | 25 | 4 | 2 | 4 | 2 | 4 |

TABLE 2-continued

Sensory test result of Preparation example 1 and Comparative example 1

| No. | Wrinkle improvement Preparation example 1 | Wrinkle improvement Comparative example 1 | Skin whitening Preparation example 1 | Skin whitening Comparative example 1 | Skin irritation Preparation example 1 |
|---|---|---|---|---|---|
| 26 | 5 | 3 | 5 | 2 | 4 |
| 27 | 5 | 2 | 5 | 3 | 5 |
| 28 | 5 | 2 | 4 | 2 | 5 |
| 29 | 4 | 2 | 5 | 3 | 5 |
| 30 | 4 | 2 | 5 | 2 | 4 |
| Total | 4.1 | 2.4 | 4.2 | 2.5 | 4.5 |

Preparation Example 2 and Comparative Example 2

By adding or not adding, as an effective component, the fusion protein (AFPSR-EGF) of antifreeze protein from sea raven and human epidermal growth factor, an essence composition was prepared with the components and content that are described in the following Table 3.

TABLE 3

Essence composition

| Component | Preparation example 2 (% by weight) | Comparative example 2 (% by weight) |
|---|---|---|
| AFPSR-EGF | 0.002 | — |
| Amino acid stock | 0.05 | 0.05 |
| Mineral mixture | 0.0007 | 0.0007 |
| Glycerol | 5 | 5 |
| 1,3-Butylene glycol | 10 | 10 |
| Carbopol 940 | 0.3 | 0.3 |
| Purified water | q.s. | q.s. |

The sensory test results using Preparation example 2 and Comparative example 2 of above Table 3 are as shown in the following Table 4.

TABLE 4

Sensory test result of Preparation example 2 and Comparative example 2

| | No. | Wrinkle improvement Preparation example 2 | Wrinkle improvement Comparative example 2 | Skin whitening Preparation example 2 | Skin whitening Comparative example 2 | Skin irritation Preparation example 2 |
|---|---|---|---|---|---|---|
| 30 s | 1 | 4 | 2 | 4 | 3 | 4 |
| | 2 | 4 | 2 | 4 | 3 | 5 |
| | 3 | 4 | 3 | 4 | 3 | 4 |
| | 4 | 4 | 2 | 3 | 3 | 4 |
| | 5 | 3 | 2 | 3 | 3 | 4 |
| | 6 | 4 | 2 | 4 | 3 | 4 |
| | 7 | 4 | 3 | 4 | 3 | 4 |
| | 8 | 3 | 2 | 4 | 3 | 4 |
| | 9 | 4 | 2 | 5 | 2 | 5 |
| | 10 | 4 | 3 | 4 | 3 | 4 |
| 40 s | 11 | 5 | 2 | 5 | 2 | 5 |
| | 12 | 5 | 3 | 5 | 2 | 5 |
| | 13 | 4 | 2 | 5 | 2 | 5 |
| | 14 | 5 | 3 | 5 | 2 | 5 |
| | 15 | 5 | 2 | 4 | 2 | 5 |
| | 16 | 5 | 2 | 4 | 2 | 4 |
| | 17 | 5 | 2 | 5 | 2 | 5 |
| | 18 | 4 | 3 | 4 | 3 | 5 |
| | 19 | 5 | 2 | 4 | 2 | 5 |
| | 20 | 4 | 3 | 5 | 2 | 5 |
| 50 s | 21 | 5 | 2 | 4 | 2 | 5 |
| | 22 | 5 | 2 | 5 | 2 | 5 |
| | 23 | 5 | 2 | 5 | 2 | 5 |
| | 24 | 4 | 2 | 4 | 2 | 5 |
| | 25 | 4 | 2 | 4 | 3 | 5 |
| | 26 | 5 | 3 | 5 | 2 | 4 |
| | 27 | 5 | 2 | 5 | 3 | 5 |
| | 28 | 5 | 2 | 4 | 2 | 5 |
| | 29 | 4 | 2 | 5 | 3 | 5 |
| | 30 | 5 | 1 | 5 | 2 | 4 |
| Total | | 4.4 | 2.2 | 4.3 | 2.4 | 4.6 |

Preparation Example 3 and Comparative Example 3

By adding or not adding, as an effective component, the fusion protein (AFPSR-EGF) of antifreeze protein from sea raven and human epidermal growth factor, a lotion composition was prepared with the components and content that are described in the following Table 5.

TABLE 5

Lotion composition

| Component | Preparation example 3 (% by weight) | Comparative example 3 (% by weight) |
|---|---|---|
| AFPSR-EGF | 0.002 | — |
| Amino acid stock | 0.05 | 0.05 |
| Mineral mixture | 0.0007 | 0.0007 |
| Glycerol | 3 | 3 |
| 1,3-Butylene glycol | 10 | 10 |
| Mineral oil | 5 | 5 |
| Cetyl alcohol | 2 | 2 |
| Xanthan gum | 0.5 | 0.5 |
| Purified water | q.s. | q.s. |

The sensory test results using Preparation example 3 and Comparative example 3 of above Table 5 are as shown in the following Table 6.

TABLE 6

Sensory test result of Preparation example 3 and Comparative example 3

| | No. | Wrinkle improvement Preparation example 3 | Wrinkle improvement Comparative example 3 | Skin whitening Preparation example 3 | Skin whitening Comparative example 3 | Skin irritation Preparation example 3 |
|---|---|---|---|---|---|---|
| 30 s | 1 | 4 | 2 | 4 | 3 | 5 |
| | 2 | 4 | 2 | 4 | 2 | 5 |
| | 3 | 4 | 3 | 4 | 3 | 4 |

TABLE 6-continued

Sensory test result of Preparation example 3 and Comparative example 3

| No. | | Wrinkle improvement Preparation example 3 | Wrinkle improvement Comparative example 3 | Skin whitening Preparation example 3 | Skin whitening Comparative example 3 | Skin irritation Preparation example 3 |
|---|---|---|---|---|---|---|
| 40 s | 4 | 3 | 2 | 3 | 3 | 4 |
| | 5 | 3 | 2 | 4 | 3 | 4 |
| | 6 | 3 | 2 | 4 | 2 | 4 |
| | 7 | 4 | 3 | 4 | 3 | 5 |
| | 8 | 3 | 2 | 4 | 3 | 4 |
| | 9 | 4 | 2 | 5 | 2 | 5 |
| | 10 | 4 | 2 | 4 | 2 | 4 |
| | 11 | 5 | 2 | 5 | 2 | 5 |
| | 12 | 5 | 3 | 5 | 2 | 5 |
| | 13 | 5 | 2 | 5 | 2 | 5 |
| | 14 | 5 | 2 | 5 | 2 | 5 |
| | 15 | 5 | 2 | 4 | 1 | 5 |
| | 16 | 5 | 1 | 4 | 2 | 4 |
| | 17 | 5 | 2 | 5 | 2 | 5 |
| | 18 | 4 | 3 | 4 | 3 | 5 |
| | 19 | 5 | 2 | 5 | 1 | 5 |
| | 20 | 5 | 1 | 5 | 2 | 5 |
| 50 s | 21 | 5 | 2 | 4 | 2 | 5 |
| | 22 | 5 | 2 | 5 | 2 | 5 |
| | 23 | 5 | 2 | 5 | 2 | 5 |
| | 24 | 4 | 2 | 4 | 2 | 5 |
| | 25 | 4 | 2 | 4 | 1 | 5 |
| | 26 | 5 | 3 | 5 | 2 | 4 |
| | 27 | 5 | 2 | 5 | 3 | 5 |
| | 28 | 5 | 2 | 5 | 2 | 5 |
| | 29 | 5 | 2 | 5 | 3 | 5 |
| | 30 | 5 | 1 | 5 | 1 | 5 |
| Total | | 4.4 | 2.0 | 4.4 | 2.1 | 4.7 |

Preparation Example 4 and Comparative Example 4

By adding or not adding, as an effective component, the fusion protein (AFPSR-EGF) of antifreeze protein from sea raven and human epidermal growth factor, a crème composition was prepared with the components and content that are described in the following Table 7.

TABLE 7

Crème composition

| Component | Preparation example 4 (% by weight) | Comparative example 4 (% by weight) |
|---|---|---|
| AFPSR-EGF | 0.002 | — |
| Amino acid stock | 0.05 | 0.05 |
| Mineral mixture | 0.0007 | 0.0007 |
| Glycerol | 2 | 2 |
| Mineral oil | 10 | 10 |
| Olive emulsion wax | 3 | 3 |
| Cetyl alcohol | 2 | 2 |
| Purified water | q.s. | q.s. |

The sensory test results using Preparation example 4 and Comparative example 4 of above Table 7 are as shown in the following Table 8.

TABLE 8

Sensory test result of Preparation example 4 and Comparative example 4

| No. | | Wrinkle improvement Preparation example 4 | Wrinkle improvement Comparative example 4 | Skin whitening Preparation example 4 | Skin whitening Comparative example 4 | Skin irritation Preparation example 4 |
|---|---|---|---|---|---|---|
| 30 s | 1 | 4 | 3 | 3 | 2 | 5 |
| | 2 | 4 | 2 | 4 | 2 | 5 |
| | 3 | 4 | 3 | 4 | 2 | 4 |
| | 4 | 4 | 2 | 3 | 3 | 4 |
| | 5 | 3 | 3 | 3 | 3 | 4 |
| | 6 | 3 | 2 | 3 | 2 | 4 |
| | 7 | 4 | 3 | 4 | 3 | 5 |
| | 8 | 4 | 2 | 4 | 3 | 4 |
| | 9 | 4 | 2 | 4 | 2 | 5 |
| | 10 | 4 | 3 | 4 | 2 | 4 |
| 40 s | 11 | 5 | 3 | 5 | 2 | 5 |
| | 12 | 5 | 3 | 5 | 2 | 5 |
| | 13 | 5 | 2 | 4 | 2 | 5 |
| | 14 | 5 | 2 | 5 | 2 | 5 |
| | 15 | 5 | 2 | 5 | 3 | 5 |
| | 16 | 5 | 2 | 4 | 2 | 4 |
| | 17 | 5 | 2 | 4 | 2 | 5 |
| | 18 | 4 | 3 | 4 | 3 | 5 |
| | 19 | 5 | 2 | 5 | 2 | 5 |
| | 20 | 5 | 2 | 4 | 2 | 5 |
| 50 s | 21 | 5 | 2 | 4 | 2 | 5 |
| | 22 | 5 | 2 | 5 | 2 | 5 |
| | 23 | 5 | 2 | 5 | 2 | 5 |
| | 24 | 4 | 2 | 5 | 2 | 5 |
| | 25 | 4 | 2 | 4 | 2 | 5 |
| | 26 | 5 | 3 | 5 | 2 | 4 |
| | 27 | 5 | 2 | 5 | 3 | 5 |
| | 28 | 5 | 2 | 5 | 2 | 5 |
| | 29 | 5 | 2 | 5 | 3 | 5 |
| | 30 | 5 | 2 | 5 | 2 | 5 |
| Total | | 4.5 | 2.2 | 4.3 | 2.2 | 4.7 |

The invention claimed is:

1. A fusion protein consisting of the amino acid sequence of SEQ ID NO: 5 or SEQ ID NO: 6.

2. A gene encoding the fusion protein of claim 1.

3. The gene according to claim 2, wherein the gene consists of any one of the nucleotide sequences of SEQ ID NOS: 1 or 2.

4. A recombinant vector comprising the gene of claim 2.

5. A host cell transformed with the recombinant vector of claim 4.

6. A method for producing a fusion protein in a host cell, the method comprising transforming the host cell with the recombinant vector of claim 4 to overexpress the gene encoding the fusion protein.

7. The method according to claim 6, wherein the host cell is *E. coli*.

8. A cosmetic composition comprising the fusion protein of claim 1, and at least one selected from the group consisting of a lipid material, an organic solvent, a dissolution agent, a condensation agent, a gelling agent, a softening agent, an anti-oxidant, a suspension agent, a stabilizer, a foaming agent, an aroma, a surface active agent, water, an ionic or non-ionic emulsifier, a filler, a metal ion sequestering agent, a chelating agent, a preservative, vitamin, a blocking agent, a moisturizing agent, essential oil, a dye, a pigment, a hydrophilic activating agent, a lipophilic activating agent, a common auxiliary agent, and a carrier.

9. The fusion protein of claim 1, wherein the amino acid sequence is SEQ ID NO: 5.

10. The fusion protein of claim 1, wherein the amino acid sequence is SEQ ID NO: 6.

11. A method for proliferating skin cells, the method comprising applying a composition comprising the fusion protein of claim 1 to the skin.

12. A method for improving skin wrinkle, the method comprising applying a composition comprising the fusion protein of claim 1 to the skin.

* * * * *

SEQUENCE LISTING

<160> NUMBER OF SEQ ID NOS: 16

<210> SEQ ID NO 1
<211> LENGTH: 549
<212> TYPE: DNA
<213> ORGANISM: Artificial Sequence
<220> FEATURE:
<223> OTHER INFORMATION: AFPSR-EGF

<400> SEQUENCE: 1

```
atgcagcgtg cacctccaaa ctgtccggca ggttggcaac cgctgggcga tcgttgtatc    60
tactatgaga ccaccgcaat gacctgggca ctggctgaaa ccaactgcat gaagctgggc   120
ggccacctgg cttctatcca gccaggaa gaacatagct ttatccagac cctgaacgcg   180
ggcgtggtct ggattggtgg tagcgcgtgc ctgcaggctg gtgcttggac ttggtccgac   240
ggtactccga tgaatttccg ctcctggtgc tccaccaaac cggacgacgt actggctgcc   300
tgttgcatgc agatgacggc ggcggccgat cagtgttggg atgacctgcc gtgcccggcg   360
tctcacaaat ctgtttgcgc catgactttc aactcagact ctgagtgccc actgtctcac   420
gacggctact gccttcacga cggagtctgc atgtacatcg aggctttgga taagtacgct   480
tgtaattgcg tcgttggtta cattggagag cgctgccaat accgtgactt aaaatggtgg   540
gagttgcgc                                                           549

<210> SEQ ID NO 2
<211> LENGTH: 549
<212> TYPE: DNA
<213> ORGANISM: Artificial Sequence
<220> FEATURE:
<223> OTHER INFORMATION: EGF-AFPSR

<400> SEQUENCE: 2
atgaactcag actctgagtg cccactgtct cacgacggct actgccttca cgacggagtc    60
tgcatgtaca tcgaggcttt ggataagtac gcttgtaatt gcgtcgttgg ttacattgga   120
gagcgctgcc aataccgtga cttaaaatgg tgggagttgc gccagcgtgc acctccaaac   180
tgtccggcag gttggcaacc gctgggcgat cgttgtatct actatgagac caccgcaatg   240
acctgggcac tggctgaaac caactgcatg aagctgggcg ccacctggc ttctatccac   300 agccaggaag aacatagctt tatccagacc ctgaacgcgg gcgtggtctg gattggtggt   360
agcgcgtgcc tgcaggctgg tgcttggact tggtccgacg gtactccgat gaatttccgc   420
tcctggtgct ccaccaaacc ggacgacgta ctggctgcct gttgcatgca gatgacggcg   480
gcggccgatc agtgttggga tgacctgccg tgcccggcgt ctcacaaatc tgtttgcgcc   540
atgactttc                                                           549

<210> SEQ ID NO 3
<211> LENGTH: 357
<212> TYPE: DNA
<213> ORGANISM: Artificial Sequence
<220> FEATURE:
<223> OTHER INFORMATION: AFPOP-EGF

<400> SEQUENCE: 3
atgaaccagg catctgtggt ggcaaaccag ctgatcccta tcaacaccgc gctgactctg    60
gtaatgatgc gcagcgaggt cgtgaccccca gttggtatcc cggctgaaga tattccgcgt   120
ctggtttcca tgcaagttaa tcgtgccgta ccgctgggca cgaccctgat gccggacatg   180
gttaaaggtt acgcggctaa ctcagactct gagtgccac tgtctcacga cggctactgc   240
cttcacgacg gagtctgcat gtacatcgag gctttggata agtacgcttg taattgcgtc   300
gttggttaca ttggagagcg ctgccaatac cgtgacttaa aatggtggga gttgcgc     357

<210> SEQ ID NO 4
<211> LENGTH: 357
<212> TYPE: DNA
<213> ORGANISM: Artificial Sequence
<220> FEATURE:
```

<223> OTHER INFORMATION: EGF-AFPOP

<400> SEQUENCE: 4

```
atgaactcag actctgagtg cccactgtct cacgacggct actgccttca cgacggagtc      60
tgcatgtaca tcgaggcttt ggataagtac gcttgtaatt gcgtcgttgg ttacattgga     120
gagcgctgcc aataccgtga cttaaaatgg tgggagttgc gcaaccaggc atctgtggtg     180
gcaaaccagc tgatccctat caacaccgcg ctgactctgg taatgatgcg cagcgaggtc     240
gtgaccccag ttggtatccc ggctgaagat attccgcgtc tggtttccat gcaagttaat     300
cgtgccgtac gctgggcac gaccctgatg ccggacatgg ttaaaggtta cgcggct        357
```

<210> SEQ ID NO 5
<211> LENGTH: 183
<212> TYPE: PRT
<213> ORGANISM: Artificial Sequence
<220> FEATURE:
<223> OTHER INFORMATION: AFPSR-EGF

<400> SEQUENCE: 5

```
Met Gln Arg Ala Pro Pro Asn Cys Pro Ala Gly Trp Gln Pro Leu Gly
1               5                   10                  15
Asp Arg Cys Ile Tyr Tyr Glu Thr Thr Ala Met Thr Trp Ala Leu Ala
                20                  25                  30
Glu Thr Asn Cys Met Lys Leu Gly Gly His Leu Ala Ser Ile His Ser
            35                  40                  45
Gln Glu Glu His Ser Phe Ile Gln Thr Leu Asn Ala Gly Val Val Trp
        50                  55                  60
Ile Gly Gly Ser Ala Cys Leu Gln Ala Gly Ala Trp Thr Trp Ser Asp
65                  70                  75                  80
Gly Thr Pro Met Asn Phe Arg Ser Trp Cys Ser Thr Lys Pro Asp Asp
                85                  90                  95
Val Leu Ala Ala Cys Cys Met Gln Met Thr Ala Ala Ala Asp Gln Cys
            100                 105                 110
Trp Asp Asp Leu Pro Cys Pro Ala Ser His Lys Ser Val Cys Ala Met
        115                 120                 125
Thr Phe Asn Ser Asp Ser Glu Cys Pro Leu Ser His Asp Gly Tyr Cys
    130                 135                 140
Leu His Asp Gly Val Cys Met Tyr Ile Glu Ala Leu Asp Lys Tyr Ala
145                 150                 155                 160
Cys Asn Cys Val Val Gly Tyr Ile Gly Glu Arg Cys Gln Tyr Arg Asp
                165                 170                 175
Leu Lys Trp Trp Glu Leu Arg
            180
```

<210> SEQ ID NO 6
<211> LENGTH: 183
<212> TYPE: PRT
<213> ORGANISM: Artificial Sequence
<220> FEATURE:
<223> OTHER INFORMATION: EGF-AFPSR

<400> SEQUENCE: 6

```
Met Asn Ser Asp Ser Glu Cys Pro Leu Ser His Asp Gly Tyr Cys Leu
1               5                   10                  15
His Asp Gly Val Cys Met Tyr Ile Glu Ala Leu Asp Lys Tyr Ala Cys
                20                  25                  30
Asn Cys Val Val Gly Tyr Ile Gly Glu Arg Cys Gln Tyr Arg Asp Leu
```

```
                35                  40                  45
Lys Trp Trp Glu Leu Arg Gln Arg Ala Pro Pro Asn Cys Pro Ala Gly
 50                  55                  60

Trp Gln Pro Leu Gly Asp Arg Cys Ile Tyr Tyr Glu Thr Thr Ala Met
 65                  70                  75                  80

Thr Trp Ala Leu Ala Glu Thr Asn Cys Met Lys Leu Gly Gly His Leu
                 85                  90                  95

Ala Ser Ile His Ser Gln Glu Glu His Ser Phe Ile Gly Thr Leu Asn
                100                 105                 110

Ala Gly Val Val Trp Ile Gly Gly Ser Ala Cys Leu Gln Ala Gly Ala
            115                 120                 125

Trp Thr Trp Ser Asp Gly Thr Pro Met Asn Phe Arg Ser Trp Cys Ser
130                 135                 140

Thr Lys Pro Asp Asp Val Leu Ala Ala Cys Cys Met Gln Met Thr Ala
145                 150                 155                 160

Ala Ala Asp Gln Cys Trp Asp Asp Leu Pro Cys Pro Ala Ser His Lys
                165                 170                 175

Ser Val Cys Ala Met Thr Phe
            180

<210> SEQ ID NO 7
<211> LENGTH: 119
<212> TYPE: PRT
<213> ORGANISM: Artificial Sequence
<220> FEATURE:
<223> OTHER INFORMATION: AFPOP-EGF

<400> SEQUENCE: 7

Met Asn Gln Ala Ser Val Val Ala Asn Gln Leu Ile Pro Ile Asn Thr
 1               5                  10                  15

Ala Leu Thr Leu Val Met Met Arg Ser Glu Val Val Thr Pro Val Gly
                20                  25                  30

Ile Pro Ala Glu Asp Ile Pro Arg Leu Val Ser Met Gln Val Asn Arg
                35                  40                  45

Ala Val Pro Leu Gly Thr Thr Leu Met Pro Asp Met Val Lys Gly Tyr
 50                  55                  60

Ala Ala Asn Ser Asp Ser Glu Cys Pro Leu Ser His Asp Gly Tyr Cys
 65                  70                  75                  80

Leu His Asp Gly Val Cys Met Tyr Ile Glu Ala Leu Asp Lys Tyr Ala
                 85                  90                  95

Cys Asn Cys Val Val Gly Tyr Ile Gly Glu Arg Cys Gln Tyr Arg Asp
                100                 105                 110

Leu Lys Trp Trp Glu Leu Arg
        115

<210> SEQ ID NO 8
<211> LENGTH: 119
<212> TYPE: PRT
<213> ORGANISM: Artificial Sequence
<220> FEATURE:
<223> OTHER INFORMATION: EGF-AFPOP

<400> SEQUENCE: 8

Met Asn Ser Asp Ser Glu Cys Pro Leu Ser His Asp Gly Tyr Cys Leu
 1               5                  10                  15

His Asp Gly Val Cys Met Tyr Ile Glu Ala Leu Asp Lys Tyr Ala Cys
                20                  25                  30
```

```
Asn Cys Val Gly Tyr Ile Gly Glu Arg Cys Gln Tyr Arg Asp Leu
         35                  40                  45
Lys Trp Trp Glu Leu Arg Asn Gln Ala Ser Val Val Ala Asn Gln Leu
 50                  55                  60
Ile Pro Ile Asn Thr Ala Leu Thr Leu Val Met Met Arg Ser Glu Val
 65                  70                  75                  80
Val Thr Pro Val Gly Ile Pro Ala Glu Asp Ile Pro Arg Leu Val Ser
                 85                  90                  95
Met Gln Val Asn Arg Ala Val Pro Leu Gly Thr Thr Leu Met Pro Asp
             100                 105                 110
Met Val Lys Gly Tyr Ala Ala
             115
```

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
atacatatgc agcgtgca                                              18

<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
gtgctcgagg cgcaactc                                              18

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
cgccatgact ttcaactcag actc                                       24

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
gtgtctgagt tgaaagtcat ggcg                                       24

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
atacatatga accaggca                                              18

```
<210> SEQ ID NO 14
<211> LENGTH: 15
<212> TYPE: DNA
<213> ORGANISM: Artificial Sequence
<220> FEATURE:
<223> OTHER INFORMATION: primer

<400> SEQUENCE: 14
tgctcgaggc gcaac                                                          15

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
tacgcggcta actcagac                                                       18

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
gtctgagtta gccgcgta                                                       18
```